(12) United States Patent
Black et al.

(10) Patent No.: US 7,291,480 B2
(45) Date of Patent: Nov. 6, 2007

(54) DEVICE AND METHOD FOR DETECTING ANTIBIOTIC-INACTIVATING ENZYMES

(76) Inventors: Jennifer A. Black, 7731 N. 159th St., Bennington, NE (US) 68007; Kenneth S. Thomson, 1282 S. 164th St., Omaha, NE (US) 68130

( * ) Notice: Subject to any disclaimer, the term of this patent is extended or adjusted under 35 U.S.C. 154(b) by 322 days.

(21) Appl. No.: 10/941,132

(22) Filed: Sep. 15, 2004

(65) Prior Publication Data

US 2005/0089947 A1    Apr. 28, 2005

Related U.S. Application Data

(63) Continuation-in-part of application No. 10/387,788, filed on Mar. 13, 2003, now abandoned.

(60) Provisional application No. 60/364,232, filed on Mar. 13, 2002.

(51) Int. Cl.
*C12Q 1/00* (2006.01)
*C12Q 1/02* (2006.01)
*C12Q 1/04* (2006.01)
*C12Q 1/18* (2006.01)

(52) U.S. Cl. .............................. 435/29; 435/32; 435/35

(58) Field of Classification Search ................. 435/4, 435/29, 32, 34

See application file for complete search history.

(56) References Cited

U.S. PATENT DOCUMENTS

| | | | |
|---|---|---|---|
| 4,492,755 A * | 1/1985 | Horwath et al. ............ | 435/94 |
| 5,338,664 A | 8/1994 | Tuckman et al. | |
| 5,466,583 A | 11/1995 | Thomson et al. | |
| 5,501,959 A | 3/1996 | Lancaster et al. | |
| 5,747,276 A | 5/1998 | Hoch et al. | |
| 5,998,159 A | 12/1999 | Watson et al. | |
| 6,242,223 B1 * | 6/2001 | Hanson et al. ............ | 435/91.2 |

OTHER PUBLICATIONS

Oliver et al., Antimicrobial Agents and Chemotherapy, Apr. 1991, vol. 43, No. 4, p. 862-867.*
Reisbig, MD & Hanson, ND The ACT-I plasmid-encoded AmpC β-lactamase is inducible: Detection in a complex beta-lactamase background. J Antimicrob Chemother (2002) 49:557-560.
Hanson, ND et al. Molecular characterization of a multiply resistant *Klebsiella pneumoniae* encoding ESBLs and a plasmid-mediated AmpC. J Antimicrob Chemother (1999) 44:377-380.
Pitout, JD et al. Modification of the double-disk test for detection of *Enterobacteriaceae* producing extended-spectrum and AmpC β-lactamases. J Clin Microbiol (2003) 41:3933-3935.
Coudron, PE et al. Occurrence and detection of AmpC beta-lactamases among *Escherichia coli, Klebsiella pneumoniae*, and *Proteus mirabilis* isolates at a veterans medical center. J Clin Microbiol (2000) 38:1791-1796.
Yong, D et al. Further modification of the Hodge test to screen AmpC β-lactamase (CMY-1)-producing strains of *Escherichia coli* and *Klebsiella pneumoniae*. J Microbiol Methods (2002) 51:407-410.
Brown DF & Brown L Evaluation of the E test, a novel method of a quantifying antimicrobial activity. J Antimicrob Chemother (1991) 27:185-190.
Thomson KS & Sanders CC Detection of extended-spectrum β-lactamases in members of the family *Enterobacteriaceae*: Comparison of the double-disk and three-dimensional tests. Antimicrob Agents Chemother (1992) 36:1877-1882.
Black, Jennifer A., et al. AmpC Disk Test for Detection of Plasmid-Mediated AmpC β-Lactamases in Enterobacteriaceae Lacking Chromosomal AmpC β-Lactamases. Journal of Clinical Microbiology, Jul. 2005, p. 3110-3113.
Rasmussen, B., et al. (1997). Carbapenem-Hydrolyzing β-Lactamases, *Antimicrobial Agents and Chemotherapy*, 41(2), 223-232.
Livermore, D. (1997). Acquired carbapenemases, *Journal of Antimicrobial Chemotherapy*, 39, 673-676.
Hirakata, Y., et al. (1998) Rapid Detection and Evaluation of Clinical Characteristics of Emerging Multiple-Drug-Resistant Gram-Negative Rods Carrying the Metallo-β-Lactamase Gene *bla*$_{imp}$ *Antimicrobial Agents and Chemotherapy*, 42(8), 2006-2011.
Arakawa, Y., et al. (2000) Convenient Test for Screening Metallo-β-Lactamase-Producing Gram-Negative Bacteria Using Thiol Compounds, *Journal of Clinical Microbiology*, 38(1), 40-43.
Walsh, T., et al. (2002) Evaluation of a New Etest for Detecting Metallo-β-Lactamase in Routine Clinical Testing *Journal of Clinical Microbiology*, 40(8), 2755-2759.

(Continued)

*Primary Examiner*—Ruth A Davis

(57) ABSTRACT

A method for determining whether a microorganism produces an AmpC β-lactamase is disclosed in which a culture of a microorganism suspected of producing a β-lactamase that inactivates a β-lactam-containing antibiotic is admixed with an effective amount of each of i) a β-lactam-containing antibiotic, ii) a β-lactamase inhibitor to which AmpC β-lactamase is resistant, and iii) a permeabilizing agent for the microorganism present in a non-growth-inhibiting microorganism-permeabilizing amount to form an assay culture. That assay culture in maintained under appropriate culture conditions and for a time period sufficient to determine the interaction of the microorganism with the AmpC β-lactamase resistant inhibitor and antibacterial compound, and thereby determine the presence of an AmpC β-lactamase, wherein a positive test indicates the presence of an AmpC β-lactamase.

15 Claims, 4 Drawing Sheets

OTHER PUBLICATIONS

Yong, D., et al. (2002) Imipenem-EDTA Disk Method for Differentiation of Metallo-β-Lactamase-Producing Clinical Isolaets of *Pseudomonas* spp. and *Acinetobacter* spp. *Journal of Clinical Microbiology*, 40(10), 3798-3801.

Walsh, T., et al. (2005). Metallo-β-Lactamases: the Quiet before Storm? *Clinical Microbiology Reviews*, 18(2), 306-325.

Hong, S., et al. (2006). Tris-EDTA (TE) Disk Test for Detection of Metallo-β-Lactamase (MBLs) in Clinical Isolates. Submitted May 2006 to http://www.icaac.org/.

Moland, E., et al. (2006). U.S. Isolate of *Kiebsiella pneumoniae* (KP) Producing VIM Metallo-β-lactamase (MBL) and SHV-5-like ESBL. Submitted May 2006 to http://www.icaac.org/.

Moland, E., et al. (2006). Simple Disk Test for Detection of Carbapenem Hydrolyzing Enzymes (CHEs). Submitted May 2006 to http://www.icaac.org/.

Hong, S., et al. (2006). Indirect Tris-EDTA (TE) Disk Test for Detection of Class A Carbapenemases in Clinical Isolates. Sumitted May 2006 to http://www.icaac.org/.

Kim, S., et al. (2006). Convenient Test Using Combination of Chelating Agents for Detection of Metallo-β-Lactamase in the Clinical Laboratory. Submitted May 2006 to http://www.icaac.org/.

Haque, H.., et al. (1975). Cell Envelopes of Gram negative Bacteria: Composition, Response to Chelating Agents and Susceptibility of Whole Cells to Antibacterial Agents, *J. appl. Bact.* 1976, 40, 89-99.

Nikaido, H., et al. (1985). Molecular Basis of Bacterial Outer Membrane Permeability, *Microbiological Reviews*, Mar. 1985, p. 1-32.

Soto, U.L., et al. (1987). Resistance of *Pseudomonas aeruginosa* to β-Lactam Antibiotics, *Folia Microbiol.* 1987, 32, 290-296.

\* cited by examiner

DEVICE AND METHOD FOR DETECTING ANTIBIOTIC-INACTIVATING ENZYMES

CROSS-REFERENCE TO RELATED APPLICATIONS

This is a continuation-in-part of application Ser. No. 10/387,788 filed on Mar. 13, 2003 now abandoned that claimed priority of U.S. Provisional Application Ser. No. 60/364,232 filed Mar. 13, 2002.

BACKGROUND OF THE INVENTION

Physicians and veterinarians often prescribe antibiotics for their sick patients on the basis of antibiotic interaction tests that presumably determine the inhibitory activity of antibiotics against the infectious microorganism. However, there can be significant problems. Sometimes a prescribed antibiotic fails to cure an infection even though the pathogen is reportedly susceptible. In serious infections, this failure can be fatal.

There can be several reasons why prescribed antibiotics fail to work, such as patient involvement, pathogen-related factors, and, most remarkably, a deficiency in the antibiotic interaction test used by the physician in selecting the appropriate antibiotic. The deficiency in the antibiotic interaction test is as follows: the test fails to account for the inactivating potential of some microorganisms toward particular antibiotics.

It is common knowledge that certain bacterial enzymes can inactivate particular antibiotics. Most notably, the β-lactamase enzymes inactivate β-lactam antibiotics, which include the most commonly prescribed antibiotics such as penicillins, cephalosporins, cephamycins, monobactams, monocarbams, penems or carbapenems (Bauernfeind et al., (1989) "Extended broad-spectrum β-lactamase in *Klebsiella pneumoniae* including resistance to cephamycins" *Infection* 17:316-321.) In choosing an effective antibiotic therapy, consideration of the presence of β-lactamase enzymes is crucial because they have been reported in infectious bacterial isolates of *E. coli, K. pneumoniae, K. oxytoca, Salmonella* spp., *Citrobacter freundii, Enterobacter aerogenes,* and *Proteus mirabilis*, to name a few. However, β-lactamase enzymes are not reliably detected in current antibiotic interaction tests. Therefore, the use of such flawed tests may lead to treatment failure and, ultimately, the resurgence of the infection in the sick patient.

At the present time, there are two conventional types of antibiotic interaction tests, disk diffusion methods or antibiotic dilution methods. In disk diffusion methods, a standard quantity of the infectious microorganism is uniformly spread over the surface of an appropriate culture medium (hereafter referred to as agar), then several filter paper disks impregnated with specific amounts of selected antibiotics are placed on the agar surface (for example see Bauer et al., (1966) *Am. J. Clin. Path.* 45:493-496; Bell, (1975) Pathology 7:Suppl 1-48; Stokes et al., (1972) Association of Clinical Pathologists Broadsheet, No. 55 (revised)). During incubation, the microorganism grows on the surface of the agar except in the areas where certain antibiotics have inhibited its growth. Inhibition of growth is detected as clear zones of no growth (inhibition zones) on the agar around the specific antibiotic disk. The sizes of the inhibition zones are measured and compared to determine the microorganism's interaction to the particular antibiotic.

On the other hand, in the dilution method, a constant quantity of microbial inoculum is introduced into a series of tubes or wells of broth containing varying concentrations of antibiotic [NCCLS (1997) "Methods for dilution antimicrobial interaction tests for bacteria that grow aerobically" Approved standard M7-A4, National Committee for Clinical Laboratory Standards, Villanova, Pa.]. After incubation, the broth tests are inspected and the lowest concentration of antibiotic that prevents detectable growth of the microorganism is recorded. This concentration is the minimum inhibitory concentration (MIC) of the antibiotic. Neither the disk diffusion nor the dilution methods provide any information regarding the presence of antibiotic-inactivating enzymes in the bacterial culture.

However, various techniques for detecting the presence of bacterial enzymes have been reported. For example, specific tests for the detection of chloramphenicol acetyltransferase, an enzyme that inactivates chloramphenicol, have been developed [Chauchereau et al., (1990) *Anal. Biochem*. 188:310-316]. These complex tests require special instruments capable of measuring the absorbance of light at specific wavelengths and/or the presence of radioactive labels. Such tests are not antibiotic interaction tests and their complexity is such that they are unsuitable for routine clinical microbiology laboratories.

A similar technique is found in the detection of the antibiotic activity of a bacterial enzyme by the production of a distinctive heaped-up margin of the inhibition zone around a penicillin antibiotic disk from the β-lactamases of *Staphylococcus aureus* [Gill et al., (1981) *J. Clin. Microbiol.* 14:437-40]. Bacterial β-lactamase production can also be detected chemically by testing the bacteria with an indicator substance such as nitrocefin [Oberhofer et al., (1982) *J. Clin. Microbiol*. 15:196-199; O'Callaghan et al., (1972) *Antimicrob. Agents Chemother*. 1:283-288]. These tests are indicators only of β-lactamase-determined resistance of *Staphylococcus aureus, Staphylococcus epidermidis, Moraxella catarrhalis, Neisseria* and *Haemophilus* species to certain types of penicillin antibiotics. They do not predict the potential for any other bacteria to resist these penicillins, nor do they predict the potential for any bacteria to be resistant to any of the other classes of β-lactam antibiotics, such as cephalosporins, cephamycins, monobactams, monocarbams, penems or carbapenems. In short, these are useful tests of limited scope. For tests of β-lactam antibiotics, a more comprehensive test is needed to detect the activities of all β-lactamases against all β-lactam antibiotics.

In another technique, disk diffusion tests were modified by a pre-incubation procedure to determine the ability of β-lactamases from *Staphylococcus aureus* to inactivate β-lactam antibiotics [Lacey et al., (1977) *J. Clin. Pathol.* 30:35-39]. This procedure results in smaller inhibition zones than those for which the interpretive criteria of the tests were calibrated. The preincubation procedure thereby invalidates the interpretive tables that are necessary to determine antibiotic interaction or resistance. This is a serious deficiency because it would be unethical to base therapy on this procedure that lacks validated interpretive criteria.

Another test is the clover leaf test which has been used to detect β-lactamases and is also claimed to detect two other types of antibiotic-inactivating enzymes, chloramphenicol acetyltransferase and erythromycin esterase [Andremont et al., (1982) "Proceedings Reunion Interdisciplinaire de Chimiotherapie Antiinfectieuse" Societe Francaise de Microbiologie, Paris:50; Kjellander et al., (1964) *Acta Path. Microbiol. Scand*. 61:494.] This test is not an antibiotic interaction test and must be set up as an additional procedure, a disadvantage for routine laboratory testing. Furthermore, there are doubts about the validity of results obtained with this procedure [Jorgensen (1985) *Chemotherapy* 31:95-101; Reig et al., (1984) *E. J. Clin. Microbiol.* 3:561-562].

Still another technique includes the cefoxitin induction test [Sanders et al., (1979) *Antimicrob. Agents Chemother.* 15:792-797] for detecting a particular type of bacterial β-lactamase, the inducible AmpC β-lactamase of Bush Group 1 [Bush et al., (1995) AAC 39:1211-1233]. This test does not detect all types of β-lactamases, and like the clover leaf test, it is a specialized and complicated procedure used to supplement antibiotic interaction tests.

Yet another technique is the double disk potentiation test which involves strategically placing an amoxicillin/clavulanate or ticarcillin-clavulanate disk at a distance of about 20 to 30 mm from disks containing cefotaxime, ceftriaxone, ceftizoxime, ceftazidime, cefepime or aztreonam on an agar plate. It is therefore possible to determine if a strain of *Enterobacteriaceae* produces a special type of β-lactamase known as an extended-spectrum β-lactamase [Brun-Buisson et al., (1987) *Lancet ii*:302-306]. The test is based on the ability of the β-lactamase inhibitor, clavulanate, to inhibit the extended-spectrum β-lactamase and prevent it from inactivating the cephalosporin or aztreonam antibiotics in the test. This is a special procedure, not a routine antibiotic interaction test, and detects only certain types of β-lactamases. It is therefore inconvenient and limited in scope.

A variety of disk and dilution tests have been derived from the principle of the double disk test [Brown et al., (2000) *J. Antimicrob. Chemother.* 46:327-328; Cormican et al., (1996) *JCM* 34:1880-1884; Ho et al., (1998) *J. Antimicrob. Chemother.* 42:49-54; Moland et al., (1998) *J. Clin. Microbiol.* 36:2575-2579; Sanders et al., (1996) *J. Clin. Microbiol.* 34:2997-3001; Schooneveldt et al., (1998) *Pathology* 30:164-168; Thomson et al., (1999) *Antimicrob. Agents. Chemother.* 43:1393-1400]. That is, they use the ability of a β-lactamase inhibitor to inhibit an extended-spectrum β-lactamase to detect this type of β-lactamase.

In another technique, the direct 3-dimensional test, [Thomson et al., (1984) *J. Antimicrob. Chemother.* 13:45-54; Thomson et al., (1992) *AAC* 36:1877-1882; U.S. Pat. No. 5,466,583], a standard quantity of the causative microorganism is uniformly spread over the surface of an agar plate in the usual manner for performing a disk diffusion test. However, before placing the antibiotic disks onto the surface of the agar, the 3-dimensional inoculation is performed. This is effected by using a sterile scalpel to cut a slit in the agar about 3 mm to one side of where the antibiotic disks will be placed. A dense liquid inoculum of the test microorganism is then dispensed into the slit, the antibiotic disks are placed on the agar 3 mm from the slit, and the test is incubated.

After incubation the inhibition zones are measured by standard procedures to determine the interaction of the microorganism to the test antibiotics according to the interpretive criteria of the disk diffusion test. However, in addition to this, enzymatic inactivation of the antibiotics can be detected by inspecting the intersections of the 3-dimensional inoculum with the margins of the inhibition zones. Antibiotic inactivation results in a distortion or discontinuity in the usually circular inhibition zone. (These distortions or discontinuities are hereafter referred to as "3-dimensional effects".)

The 3-dimensional test thus permits the laboratory to report to the clinician not only the interaction or resistance of a microorganism to antibiotics, but also the ability of the microorganism to inactivate the antibiotics. As a hypothetical example, whereas a conventional antibiotic interaction test might indicate that a microorganism was susceptible to the two antibiotics, cefaclor and cefoxitin, the 3-dimensional test can provide additional information to show that the microorganism produced an enzyme capable of inactivating cefaclor but not cefoxitin. Thus, although the conventional test indicated that both antibiotics appeared to be equally efficacious, it would appear, from the additional information provided by the 3-dimensional test, that only cefoxitin might not be inactivated in the patient and therefore would constitute a more effective treatment than cefaclor. In this example, the information provided by the 3-dimensional test could assist a clinician to make a better choice of therapy.

In addition to the direct form of the 3-dimensional test, an indirect form is used for testing microorganisms when inhibition zones are small or absent, or as a research or diagnostic method. The indirect test is performed by inoculating the surface of the agar with a fully susceptible assay strain such as *Escherichia coli* ATCC 25922. After this, the 3-dimensional slit is cut in the agar and inoculated with a suspension of the test microorganism. Although the indirect test precludes the simultaneous determination of antibiotic susceptibilities, it permits investigation of the antibiotic inactivating enzymes of microorganisms for which the inhibition zones are too small to yield 3-dimensional results when the test is performed in the direct form of the test.

There are several problems with the 3-dimensional test. These problems include the following:
  a) The procedure for making the slit in the agar for the 3-dimensional test is inconvenient and technically difficult to perform correctly;
  B) Making the slit is potentially dangerous to laboratory staff because a scalpel blade contaminated with pathogenic bacteria is an infection hazard; and
  c) It is also technically difficult to accurately deliver the liquid 3-dimensional inoculum into the slit without overfilling the slit and possibly invalidating the test.

As disclosed hereinafter, the present invention provides one solution to the problems of current antibiotic interaction tests used by the physician in selecting the appropriate antibiotic. The present invention provides an effective method for evaluating the inactivating potential of some microorganisms toward particular antibiotics.

BRIEF SUMMARY OF THE INVENTION

The present invention contemplates a method of determining whether a microorganism produces an AmpC β-lactamase. In accordance with that method, a) a culture of a microorganism suspected of producing a β-lactamase that inactivates a β-lactam-containing antibiotic such as cefoxitin is admixed with an effective amount of each of i) a β-lactam-containing antibiotic such as cefoxitin, ii) a β-lactamase inhibitor to which AmpC β-lactamase is resistant, e.g., clavulanate, sulbactam or tazobactam, and iii) a permeabilizing agent for the microorganism present in a non-growth-inhibiting microorganism-permeabilizing effective amount to form an assay culture. That assay culture in maintained (incubated) under appropriate culture conditions and for a time period sufficient to determine the interaction of the microorganism with the AmpC β-lactamase resistant inhibitor and antibacterial compound, and thereby determine the presence of an AmpC β-lactamase, wherein a positive test (a lack of inhibition of microbial growth) indicates the presence of an AmpC β-lactamase. That assay culture in maintained (incubated) under appropriate culture conditions and for a time period sufficient to determine the interaction of the microorganism with the AmpC β-lactamase resistant inhibitor and antibacterial compound, and thereby the determine presence or absence of an AmpC β-lactamase, wherein a positive test (a lack of inhibition of microbial growth) indicates the presence of an AmpC β-lactamase and a negative test (inhibition of microbial growth) indicates the absence of an AmpC β-lactamase.

In preferred embodiments, the β-lactamase inhibitor is clavulanate, sulbactam or tazobactam, with clavulanate being particularly preferred). It is also preferred that the β-lactamase inhibitor be present in an amount of about 5 to about 250 μg per standard interaction test disk and more usually about 5 to about 50 μg, or in a proportional amount if a different assay format is utilized.

It is further preferred that the permeabilizing agent be dissolved or dispersed in a carrier. In preferred embodiments, the permeabilizing agent dissolved in a carrier is an aqueous buffer solution. A preferred buffer solution is Tris/EDTA (TE). The carrier can be a solid carrier. A preferred solid carrier is a paper disk, as is an above standard interaction test disk. Alternatively, the carrier can be a liquid carrier. In such embodiments, the permeabilizing agent dissolved in a carrier is an aqueous buffer solution. Where a solid paper disk and an aqueous liquid carrier are present, the solid paper disk is deemed to be the carrier and the liquid phase is deemed to be part of the culture medium for the assayed microorganism.

In another embodiment, the culture is provided on a solid growth medium. Alternatively, the culture is provided in a liquid growth medium.

In a further embodiment, the carrier is a solid carrier, the culture is provided on a solid growth medium, the antibiotic is provided on a solid support, and the admixing is done by contacting the culture with the solid carrier and the antibiotic provided on a solid support.

As can be readily seen, the invention provides several novel benefits and advantages over other antibiotic-sensitivity testing methods. Thus, in one benefit, the invention permits AmpC β-lactamase testing to be performed in the presence of other β-lactamases. That testing can be carried out on the surface of the agar, rather than the technically challenging aspect of some other methods that require the insertion of bacterial inoculum into a slit in the agar.

Furthermore, the invention contemplates the advantage of use of a permeabilizing agent that facilitates the release of antibiotic inactivating factors from microorganisms, without significantly inhibiting the growth of those microorganisms. The present invention provides more robust in vitro information that can detect microorganisms that are likely to produce AmpC β-lactamase and be resistant to a particular antibiotic in vivo.

BRIEF DESCRIPTION OF THE DRAWINGS

In the drawings forming a portion of this disclosure.

DETAILED DESCRIPTION OF THE INVENTION

Figure 1:
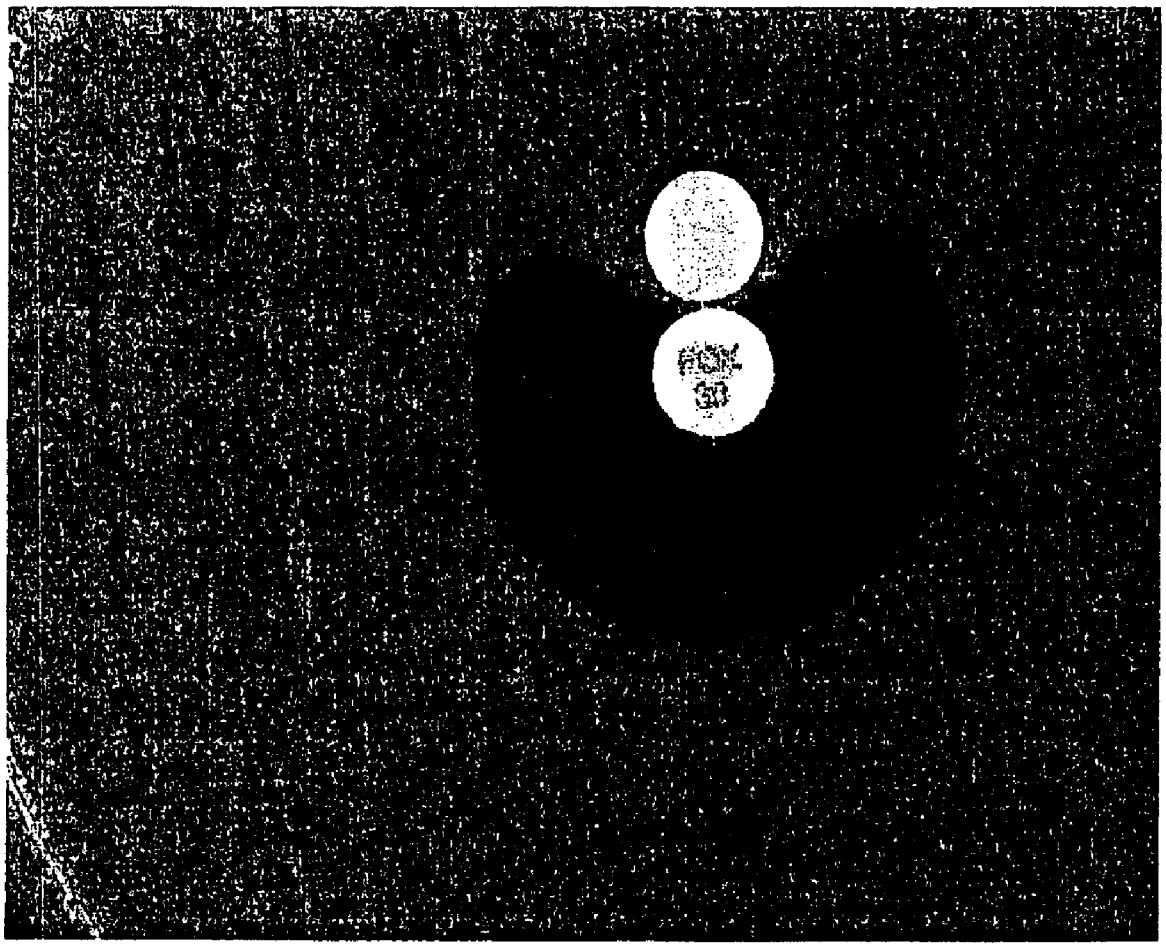
FIG. 1 shows a close up of a zone of distortion surrounding a cefoxitin disk.

The present invention provides a method to identify microbes that produce AmpC β-lactamase that may be present in a microbial culture. That method is typically carried out in the context of determining the antibiotic interaction of a microorganism based upon increasing the permeability of the cell wall and/or cell membrane(s) of a microorganism by incubating a microorganism in the presence of a permeabilizing agent. The permeabilizing agent is preferably present in an amount that neither kills the microorganism nor significantly inhibits its ability to replicate, but nevertheless permeabilizes the microorganism. While not wishing to be bound by theory, it is believed that the presence of an appropriate concentration of permeabilizing agent permits the enhanced liberation or release of antibiotic-inactivating factors (e.g., AmpC β-lactamase enzymes) from the microorganism. The liberation or release of such antibiotic-inactivating factors permits a microorganism to grow in the presence of the antimicrobial agent and AmpC β-lactamase resistant inhibitor.

More particularly, a method of the present invention contemplates the steps of admixing a) a culture of a microorganism suspected of producing a β-lactamase that inactivates a β-lactam-containing antibiotic such as cefoxitin with an effective amount of each of i) a β-lactam-containing antibiotic such as cefoxitin, ii) a β-lactamase inhibitor to which AmpC β-lactamase is resistant, e.g., clavulanate, sulbactam or tazobactam, and iii) a permeabilizing agent for the microorganism present in a non-growth-inhibiting microorganism-permeabilizing effective amount to form an assay culture. That assay culture in maintained (incubated) under appropriate culture conditions and for a period of time sufficient to determine the interaction of the microorganism with the AmpC β-lactamase resistant inhibitor and antibacterial compound, and thereby determine the presence of an AmpC β-lactamase, wherein a positive test (a lack of inhibition of microbial growth) indicates the presence of an AmpC β-lactamase, and a negative test (inhibition of microbial growth) indicates the absence of an AmpC β-lactamase.

Exemplary β-lactam-containing antibiotics such as cefoxitin include cefotetan, nitrocefin, cefaclor, and the like as are well known. Further cephamycin-, carbapenem-, carbacephem-, monobactam-, penicillin- and cephalosporin C-type β-lactam-containing antibiotics can be found in the 2002 USP Dictionary of USAN and International Drug Names, U.S. Pharmacopeia, Rockville, Md. (2002). A single antibiotic can be used, or a mixture of antibiotics can be used. Amounts of individual β-lactam-containing antibiotics effective to inhibit the growth of microbes to be assayed can be readily determined using the MIC determination discussed elsewhere herein as well as from the commercially available assay disks available from Fisher Scientific, Hanover Park, Ill. USA under the designation BD BBL Sensi-Disc™ susceptibility test disks or Oxoid® susceptibility test disks (manufactured Basingstoke, Hampshire, UK) available from Remel Co., (Lenexa, Kans.).

Illustrative AmpC β-lactamase-resistant inhibitor compounds include clavulanate, sulbactam and tazobactam. Clavulanate is preferred. These compounds can inhibit the KPC-1, KPC-2 and some CTX-M β-lactamase enzymes, but they do not inhibit AmpC β-lactamase. The amount of such β-lactamase inhibitors to be added to a standard susceptibility test disk is about 5 to about 250 μg, and preferably about 5 to about 50 μg, and more preferably about 10 to about 30 μg. Useful amounts of inhibitor can be determined for other systems based upon the amount used in an above system.

A permeabilizing agent can be used to detect antibiotic-resistant microorganisms (microorganisms with the potential to express antibiotic resistance during therapy) that would otherwise register as falsely sensitive to a test antibiotic, by facilitating the liberation or release of antibiotic-inactivating factors. Surprisingly, although microbial growth in the presence of the permeabilizing agent is not required, the microorganism can often grow in the presence of a permeabilizing agent that is normally lethal to a microorganism, or inhibits the growth of a microorganism.

Thus, the invention comprises the use of a permeabilizing agent, in a non-growth-inhibiting, microorganism-permeabilizing effective amount. As set forth in more detail elsewhere herein, determining a non-growth-inhibiting amount of a permeabilizing agent is a matter of routine experimentation involving the titration of the permeabilizing agent for its ability to significantly inhibit microorganism growth. Similarly, the determination of a microorganism-permeabilizing effective amount of a permeabilizing agent is a matter of routine experimentation involving the titration of the permeabilizing agent for its ability to permeabilze a microorganism, such as by liberation of antibiotic-inactivating factors from a known antibiotic-resistant strain of a test microorganism.

The permeabilizing agent, in the effective amount set forth herein, is admixed with a culture of a microorganism whose production of AmpC β-lactamase is to be determined. The culture is prepared according to methods that are well known in the art, such as by introducing an inoculum of the microorganism (such as from a clinical sample) into an appropriate growth medium. The growth medium can be a liquid growth medium, such as Luria or Meuller-Hinton broths, or a sold growth medium, such as an agar plate supplemented with necessary nutrients, such as a Mueller-Hinton agar plate.

Antibiotic-interaction assays are set forth elsewhere herein, and are not meant to be limiting with respect to such assays that can be adapted for use in the instant invention. The culture is also admixed with the permeabilizing agent.

If needed, a control, without one or more of the AmpC β-lactamase inhibitor, antibiotic or permeabilizing agent can be prepared under similar conditions. Where the admixture is done with a liquid growth medium and a permeabilizing agent in a liquid carrier, as described elsewhere herein, serial dilutions of the antibiotic to be assayed are prepared in the liquid growth medium. Parallel samples are admixed with or without the permeabilizing agent in the liquid carrier. An antibiotic that at a particular antibiotic dilution exhibits antimicrobial activity in the absence of permeabilizing agent, but is ineffective at that dilution in the presence of permeabilizing agent, is considered likely to be ineffective against the assayed microorganism, on the basis that the microorganism liberates a factor that inactivates that antibiotic.

The thus prepared culture is then incubated under appropriate culture conditions and for a time sufficient to determine the interaction of the microorganism to the antibiotic or antibiotics of interest. For example, an agar plate can be incubated at 35 degrees Celsius for 12 to 18 hours in an environmentally controlled incubator. A culture in a liquid medium can be incubated in a shaking water bath at 35 degrees Celsius for 12 to 18 hours on a bench top. The appropriate culture conditions and sufficient times are well known to workers of ordinary skill in the art.

As noted, the permeabilizing agent can be provided in a liquid or a solid carrier, dispersed or dissolved therein. For example, in the case of a liquid permeabilizing agent, such as a buffer solution, the buffer solution is itself in a liquid carrier. Alternatively, a detergent can be dispersed in an aqueous medium, or in growth broth, for use in the methods of the invention.

Exemplary permeabilizing agents useful in the present invention include those agents that increase the permeability of the cell wall and/or cell membrane(s) of a microorganism, but that are present in amounts or concentrations that do not significantly inhibit the growth or reproduction of the assayed microorganism. As is well known to those of ordinary skill in the art, not all microorganisms possess both a cell wall and a cell membrane; moreover, those microorganisms that possess both a cell wall and a cell membrane do not have walls or membranes that are structurally identical. For example, bacteria are broadly categorized as Gram-positive or Gram-negative based upon their cell wall/cell membrane structure. A permeabilizing agent useful in the present invention preferably permeabilizes the cell surface structure (cell wall or cell membrane, or both) such that antibiotic-inactivating factors are liberated from the cell. However, it is also preferred that the permeabilizing agent not kill or significantly inhibit the growth of the microorganism.

Specific exemplary permeabilizing agents include the following:

Inorganic salts, such as sodium chloride (NaCl), magnesium chloride ($Mg_2Cl$), potassium chloride (KCl) and the like;

Quaternary ammonium compounds such as benzalkonium chloride (BAC), cetylpyridium chloride, 3-(trimethoxysilyl) propyldimethyloctadecyl ammonium chloride and the like;

Buffer solutions, such as Tris/EDTA (TE) buffer, NaCl/Tris/EDTA (STE) buffer, glucose/Tris/EDTA (GTE) buffer, and the like;

Hypotonic or hypertonic agents, such as sugar solutions, including glucose, dextrose, sucrose, fructose, lactose and the like;

Antibiotics such as Piperacillin, Aztreonam, Amdinocillin, Ceftazidime, Polymyxin B, Polymyxin B nonapeptide, or Gentamicin, and the like used at a sub-lethal dose.

Commercially available detergent or surfactant-containing agents such as Blind Brite™, Maxaquin™, HyVee Glass Cleaner™, Life Tree™, Rave™, Dawn™, and the like;

Other commercially available materials such as Isoclean concentrate, Sight Savers™ lens cleaner, Wash™ (green handwash), Micro Lab Cleaning Solution™, Jet Clean™ test tube cleaner, Limonene™, and the like;

Other surfactants and/or detergents such as Triton® X-100, sodium dodecyl sulfate (SDS), SDS (5%) mixed with acetone, Sarcosyl™, Sarcosyl™ mixed with acetone, Tween® (polysorbate) 80, Tween® 80 mixed with acetone, Tween® 85, Brij® 56, polyethylene glycol, polypropylene glycol, dansyl-polymyxin and the like.

Other exemplary permeabilizing agents include CHAPS (3-[(3-cholamidopropyl)-dimethyl-ammonio]-1-propane-sulfonate) electrophoresis reagent, $\leq 10$ mM (Sigma cat # C-9426), lactic acid, and sodium hexametaphosphate (sodium polyphosphate) (chelating agent).

Natural peptide agents such as cecropins (cationic peptides), melittin (cationic peptide), bactenecin, magainins (frog host defense peptides), tachyplesins (cationic peptides), polyphemusins (cationic peptides), and synthetic peptides and the like can also be used as preferred permeabilizing agents.

A preferred permeabilizing agent is Tris/EDTA (TE) buffer, commercially available from Sigma-Aldrich (catalog number T-9285). As supplied, the TE buffer is at a 100× concentration, comprised of 1.0 molar Tris-HCl (pH approximately 8.0) and 0.1 molar EDTA. The TE buffer is preferably placed onto a disk at a concentration of 100 millimolar, 200 millimolar, 0.5 molar, 1 molar, 2 molar or 10 molar. The TE buffer is further preferably placed onto a disk at a concentration of 100×, 50×, 25× and 10×. Methods for determining the optimal concentration of a particular permeabilizing agent are given elsewhere herein.

As noted elsewhere herein, a permeabilizing agent preferably permits or facilitates the release of AmpC β-lactamase enzymes from within a microorganism while not significantly inhibiting the growth of that microorganism. The ability of a permeabilizing agent to liberate or release AmpC β-lactamase enzymes from a microorganism can be determined by, for example, quantitation of the amount of AmpC β-lactamase enzymes, released. Such quantitation can be determined by, for example, spectrophotometric hydrolysis assays using either nitrocefin or cefaclor as substrates. The ability of a permeabilizing agent to liberate or release AmpC β-lactamase enzymes from a microorganism can also be determined by, for example, antibiotic-sensitivity tests such as the 3-dimensional test discussed elsewhere herein. Exemplary determinations of the ability of a permeabilizing agent to liberate or AmpC β-lactamase enzymes from a microorganism are described in the Examples set forth hereinafter.

A preferred permeabilizing agent also does not significantly inhibit the growth of a microorganism. This property of a preferred permeabilizing agent can be determined by, for example, applying varying concentrations of a particular permeabilizing agent to lawn cultures of a variety of microorganisms to determine if inhibition of growth of the lawn culture occurred. Alternatively, the growth rates of various microorganisms in the presence of varying concentrations of a permeabilizing agent can also be determined, using techniques well known in the art. Exemplary determinations of the ability of a permeabilizing agent to permit the growth of a microorganism are described in the Examples set forth elsewhere herein.

In some aspects of the invention, the permeabilizing agent is provided on a solid support. For example, the buffer solution can be impregnated onto a solid support such as a piece of filter paper. The filter paper is then left to dry, and the permeabilizing agent is dispersed onto the solid carrier.

In one embodiment, the impregnated disk is used in an antibiotic sensitivity assay to permeabilize the microorganism whose antibiotic sensitivity is being measured, without killing or significantly inhibiting the growth of the microorganism. An appropriate amount (concentration) of a permeabilizing agent to be used in preparing these impregnated disks can be determined to effect liberation of antibiotic-inactivating factor(s) from a microorganism, without killing or inhibiting the growth of a microorganism.

The invention is designed to increase the amount of information provided by laboratory tests in which the production of AmpC β-lactamase is evaluated by disk diffusion methods or by other well-known methods. The invention provides a means to routinely detect the ability of microorganisms to produce particular β-lactamase enzymes. The information can be useful in selecting appropriate anti-infective therapies for the treatment of infections, in providing epidemiological information about microorganisms, in antibiotic research, and in other fields of biological research such as genetics and enzymology.

In a preferred embodiment, the invention comprises providing a filter paper disk impregnated with a β-lactam-containing antibiotic such as cefoxitin that facilitates the production and release of AmpC β-lactamase enzymes from bacteria or other microorganisms, β-lactamase inhibitor to which AmpC β-lactamase is resistant and permeabilizing agent. This impregnated filter paper disk is sometimes referred to herein as the reagent disk. Typically, the permeabilizing agent in the reagent disk disrupts the outer membrane, or both the outer and cytoplasmic membranes of a microorganism such as a bacterium to release AmpC β-lactamase enzymes from within the microorganism. In a preferred method of the invention, a disk impregnated with a permeabilizing agent is provided, such as a BD BBL Sensi-Disc™ interaction test disk discussed before.

A suitable growth-medium-containing agar plate is inoculated with a lawn of test microorganism (e.g., a clinical sample, or a strain of bacteria for which the presence of AmpC β-lactamase is to be determined). An antibiotic-impregnated reagent disk (e.g., containing cefoxitin) that also contains a β-lactamase inhibitor to which AmpC β-lactamase is resistant (e.g., clavulanate, tazobactam or sulbactam) and permeabilizing agent (e.g., TE) is placed onto the lawn of microorganism. The test microorganism is additionally inoculated onto a provided reagent disk, and that reagent disk is placed on the agar adjacent to, but not in contact with, an antibiotic disk of interest. Alternatively, and preferably, the permeabilizing agent and the β-lactamase inhibitor are in a different disk from the antibiotic disk. The agar plate is then incubated (maintained) according to methods well known in the art.

After incubation, the results are interpreted as follows. AmpC β-lactamase enzymatic inactivation of an antibiotic can be detected by inspecting the margin of the inhibition zone in the vicinity of the reagent disk. Antibiotic inactivation results in a distortion in the usually circular zone of inhibition. The presence of this distortion indicates that the test microorganism produces AmpC β-lactamase that inactivates cephalosporins, cephamycins, monobactams, carbacephems, and penicillins. From a clinical perspective, the use of an antibiotic that exhibits a zone of distortion would be contraindicated for treatment of an infection with the test microorganism.

It should be understood that although a preferred embodiment of the invention is as described above, the invention is not limited to that embodiment. Solid carriers other than a filter paper disk, such as filter paper strips, pieces of nitrocellulose, or other carriers can be used as a vehicle to effect contact between the microorganism and the reagent. Test methodologies other than the disk diffusion test, such as the E test [Brown et al., *J. Antimicrob. Chemother*. 27:185-190 (1991)], or the dilution methods can also be modified for detection of antibiotic inactivating enzymes without departing from the spirit and scope of the invention.

In a further embodiment, the invention comprises an indirect form for testing microorganisms when inhibition zones are small or absent, or as a research or diagnostic method. The indirect form of test is performed by inoculating the surface of the agar with a fully antibiotic-susceptible assay strain such as *Escherichia coli* ATCC 25922. After this, the provided reagent disk is inoculated with a suspension of the test microorganism (e.g., a clinical isolate) and the test performed as described above except that the assay strain, e.g., *E. coli* ATCC 25922, grows on the surface of the agar instead of the causative organism. This indirect form of a method of the invention permits investigation of the AmpC β-lactamase enzymes of microorganisms for which the inhibition zones are too small to yield results when the test is performed in the direct form of the test.

In another embodiment, the present invention comprises a kit comprising a permeabilizing agent-impregnated disk and instructions for performing an antibiotic sensitivity test to detect microorganisms that liberate antibiotic-inactivating factors. In a preferred embodiment, the permeabilizing agent is Tris/EDTA buffer (TE).

EXAMPLES

Example 1

Determination of Release of Antibiotic-Inactivating Factors

In this Example, *E. coli* MISC 208 (which produces the extended spectrum β-lactamase SHV-2) was used as a test organism and nitrocefin was the substrate in spectrophotometric hydrolysis assays. The *E. coli* strain was harvested directly into 100 microliters of Mueller Hinton Broth and mixed with 100 microliters of the permeabilizing agent.

In the hydrolysis assay, units of activity are calculated as:

$$\text{Units} = \frac{\text{Change in optical density } (OD)/\text{minute} \times 10}{\text{Extinction coefficient}}$$

The hydrolysis assay was performed essentially as described by O'Callaghan et al., *A.A.C.* 1:283-288 (1972). Briefly, a 100 µM solution of nitrocefin was used as a substrate. The nitrocefin was prewarmed to 37° C. The hydrolysis assay was performed at 37° C. at a wavelength of 389.5 with an extinction coefficient of −0.024. An appropriate cuvette was filled with 0.9 ml of the prewarmed nitrocefin substrate and 100 µl of permeabilized bacterial suspension was added. The contents of the cuvette were immediately mixed by inversion and the cuvette was placed in a spectrophotometer. Absorbance was assayed at 5-second intervals for up to 5 minutes with the 37° C. temperature maintained by means of a circulating water bath that warmed the cuvette block. When the assay was complete, the activity was calculated according to the above formula. The results are shown I the Table below.

| Permeabilizing Agent Preparation | Units of β-lactamase Activity |
|---|---|
| (Nitrocefin as substrate) | |
| TE*/Room temp | 47 |
| TE*/0° C. | 102 |
| Tris/0° C. | 41 |
| Water (control) | 0 |

*TE = Tris/EDTA

Example 2

Determination of Release of Antibiotic-Inactivating Factors

The experiment in Example 1 was repeated using *E. coli* MISC 208 and cefaclor as substrate in the hydrolysis assays.

| Permeabilizing Agent Preparation | Units of β-lactamase Activity |
|---|---|
| (Cefaclor as substrate) | |
| Benzalkonium chloride 200 µg/ml | 16 |
| Polymyxin B 10 µg/ml | 3.8 |
| Polymyxin B 30 µg/ml | 15 |
| TE | 79 |

Example 3

Determination of Release of Antibiotic-Inactivating Factors

The study in Example 1 was repeated using *E. coli* V1104 to evaluate a variety of permeabilizing agents. Nitrocefin was the hydrolysis substrate.

| Permeabilizing Agent Preparation | Units of β-lactamase Activity |
|---|---|
| (Nitrocefin as substrate) | |
| Aztreonam | 210 |
| No reagent/0° C. | 214 |
| No reagent/45° C. | 0 |
| Ceftazidime | 196 |
| Piperacillin | 202 |

Other exemplary microorganisms that can be used in the determination of release of antibiotic-inactivating factors include those in the following Table:

| Strain | Enzyme | Units (vs nitrocefin) |
|---|---|---|
| *E. coli* V1104 | | 202 |
| *E. coli* 165* | pI 5.95 TEM ESBL | 43 |
| MG32 | TEM-1 + TEM-12 | 349 |
| *K. pneumoniae* V1102 | | 227 |

Example 4

Determination of Lack of Significant Growth Inhibition

A variety of test strains have been harvested directly into 100 microliters of Mueller-Hinton Broth and mixed with 100 microliters of each permeabilizing agent of interest. Then, 20 microliters of each of these mixtures was applied to blank filter paper disks, and the disks transferred to freshly inoculated agar lawn cultures of a variety of test microorganisms and the plates were incubated at 37° C. for about 16 hours. After that incubation, the cultures were inspected for the presence or absence of an inhibition zone around the disk. An inhibition zone implied unsuitability of the permeabilizing agent for the test at the concentration used.

In a variant of this method, the reagent is applied directly to a disk without previously mixing the reagent with a microorganism, with the evaluation as above.

Making the Reagent Disk

A solution of equal parts of physiological saline and Tris EDTA (Sigma Chemicals) is made.
1. A 20 microliter aliquot of the permeabilizing agent solution was placed onto a filter paper disk and allowed to dry.

Figure 2:
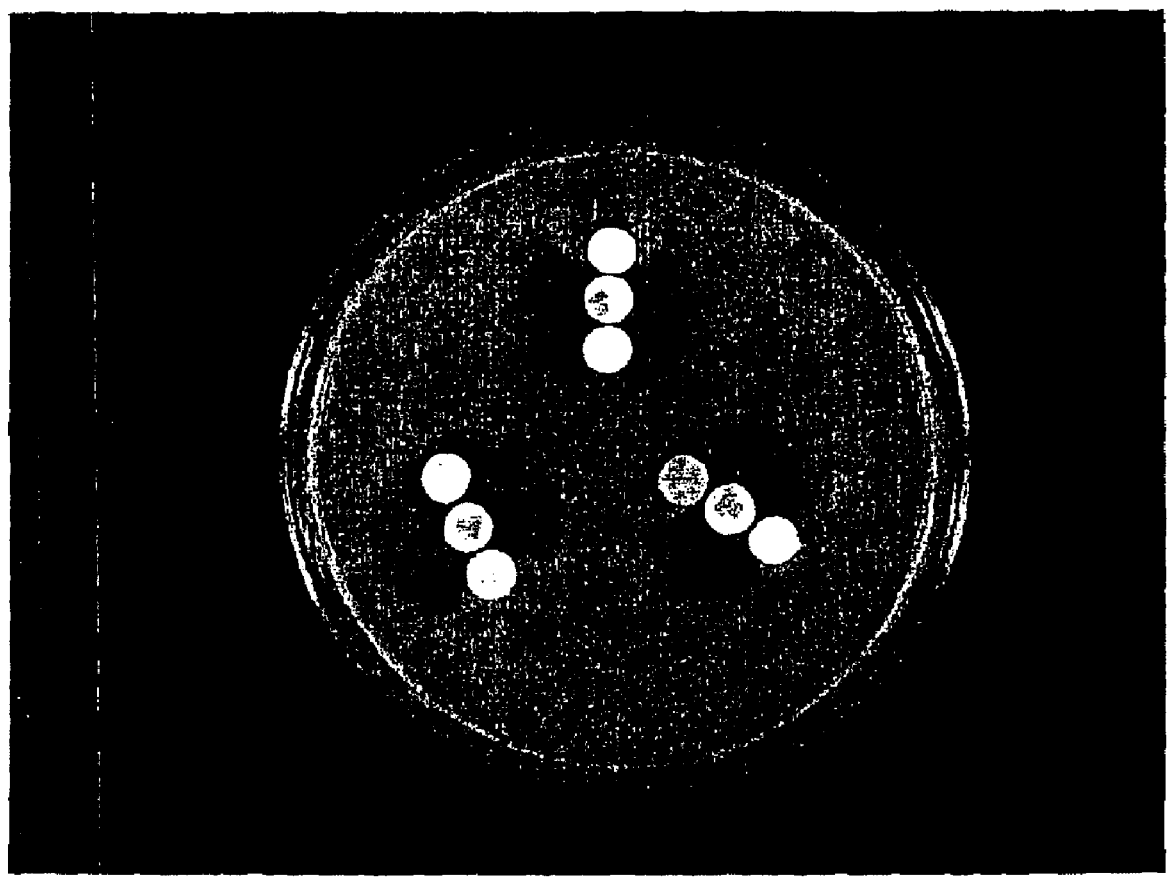
FIG. 2 shows one embodiment of the invention in which the indirect form of a method of the invention is shown in the testing of five test microorganisms and a negative control organism. In this assay the fully susceptible strain E. coli ATCC 25922 was used as the lawn culture to assay for inactivating factors produced by the test and control microorganisms. Three commercially manufactured cefoxitin disks (labeled FOX 30) are bracketed by the reagent test disks. A test or control organism was applied to each of the reagent disks prior to their placement proximal to the cefoxitin disks. Strong indentations of the inhibition zone margins indicate inactivation of cefoxitin by inactivating factors released from the test microorganisms subsequent to encountering the permeabilizing agent in the disks. The negative control has no distortion (bottom disk of top set of 3 disks with orientation pointing to 12 o'clock). A weakly positive test occurred at the disk closest to 9 o'clock (shown as slight flattening or blunting of the inhibition zone margin). This result was obtained with a strain of Klebsiella pneumoniae previously determined to be a low level producer of a cefoxitin-inactivating β-lactamase. (This strain is a potential candidate as a quality control strain associated with the threshold of sensitivity of detection of the test for this particular antibiotic inactivating factor).

Performing and Interpreting the Test
1. The filter paper disk impregnated with the permeabilizing agent was rehydrated with 20 microliters of sterile physiological saline.
2. Using a cotton swab or loop, a test organism was rubbed onto the rehydrated disk.
3. A Mueller Hinton Agar plate was inoculated with a 0.5 McFarland of *E. coli* ATCC 25922.
4. A cefoxitin disk was placed onto the surface of the agar plate. The rehydrated disk inoculated with the test organism next was placed next to the cefoxitin disk, at a distance of about 0.5-1.0 mm.
5. The agar plate was incubated at 37° C. for about 16 hours, or overnight.
6. Distortion of the cefoxitin zone was interpreted as a positive result (i.e., the presence of an antibiotic-inactivating factor was detected), whereas lack of distortion of the cefoxitin zone was interpreted as a negative result. See FIGS. 1 and 2.

Example 5

Detection of Antibiotic-Resistant Microorganisms

This study reports its utility for investigation of *Klebsiella* isolates suspected of harboring pAmpC enzymes.

Methods:

Thirty isolates of *Klebsiella* spp. with cefoxitin minimal inhibitory concentrations (MICs) of grater than 16 micrograms per milliliter were investigated using the methods of the invention. All negative results were confirmed with the three-dimensional test, discussed elsewhere herein, and positive results were confirmed by isoelectric focusing (IEF) and inhibitor studies. A filter paper disk was impregnated with 100× TE that had been diluted with an equal volume of physiological saline. The disk was rehydrated with 20 microliters of saline and several colonies of the test isolate were inoculated onto the disk. The inoculated disk was then placed beside a cefoxitin disk (almost touching) on a Mueller-Hinton agar plate inoculated with a lawn of *E. coli* ATCC 25922. After overnight incubation (about 16 hours), a positive test appeared as a flattening or indentation of the cefoxitin inhibition zone near the test disk. A negative test had an undistorted zone.

Results:

Of the 30 isolates assayed, 10 were positive and 20 were negative (also negative with the three-dimensional test). IEF and inhibitor studies of the positive isolates indicated that 9 of the 10 isolates produced β-lactamases that were inhibited by cloxacillin with pIs of either 7.2, 7.7 or more than 9.0, findings consistent with AmpC production. These enzymes were interpreted to be plasmid-mediated because *Klebsiella* lacks a chromosomal AmpC. The other positive isolate had an elevated imipenem MIC and produced a carbapenem-hydrolyzing enzyme that also hydrolyzed cefoxitin.

MATERIALS AND METHODS

Isolates

Thirty recent isolates of *Klebsiella* spp. were collected from patients in United States hospitals.

Interaction

Antimicrobial interaction was determined by NCCLS microdilution methodology using an investigational Microscan dehydrated panel.

Three-Dimensional Test

Figure 3:
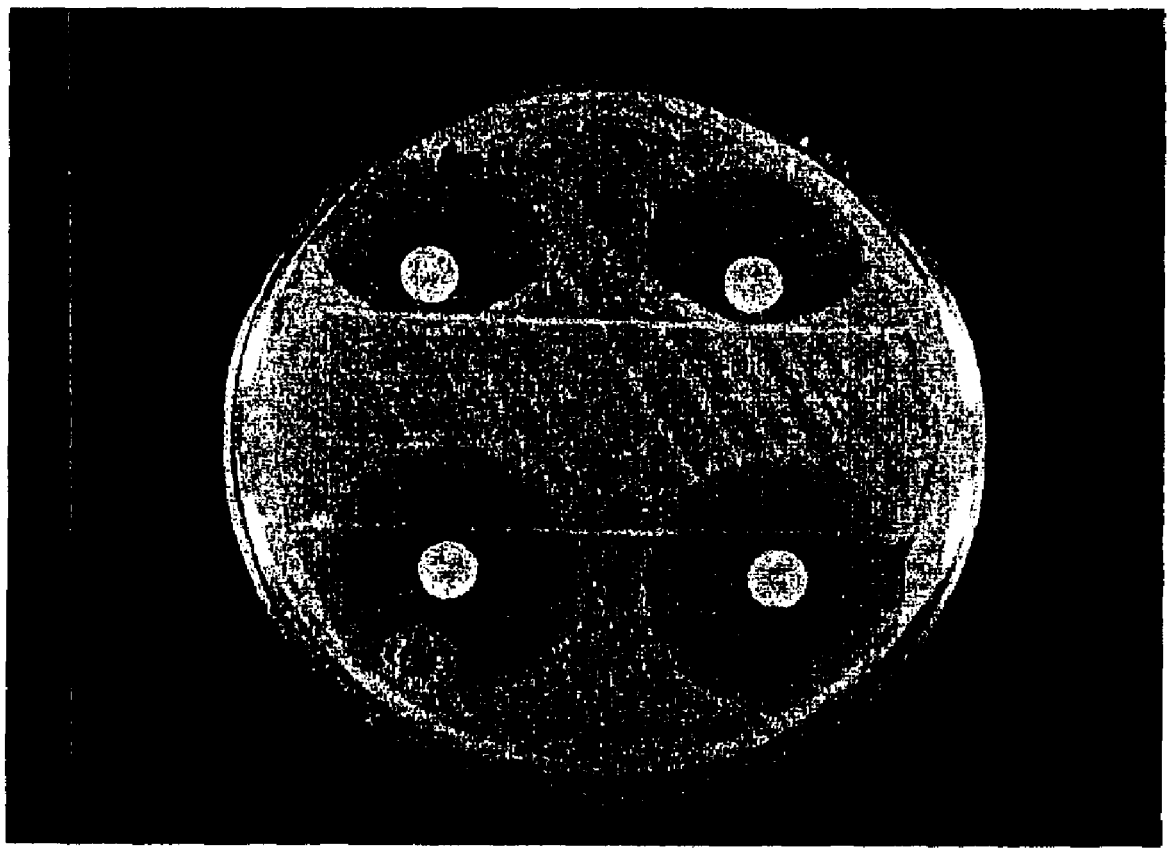
FIG. 3 shows a three-dimensional test demonstrating the enzymatic inactivation of cefoxitin by a strain of Klebsiella.

Enzymatic inactivation of cefoxitin was investigated by the three-dimensional method. The surface of a Mueller-Hinton agar plate was inoculated with a lawn of a standardized inoculum of *E. coli* ATCC 25922. A slit was then cut into the plate with a sterile scalpel blade. Into the slit, a suspension containing a heavy inoculum ($10^9$ CFU per milliliter) of the test organism was dispensed by capillary action from a micropipette tip. A cefoxitin disk was then placed on the agar 3 millimeters from the slit. After overnight incubation (about 16 hours) at 35 C, the plate was examined for evidence of cefoxitin inactivation, as indicated by a characteristic distortion of the inhibition zone margin. The absence of this feature indicated no significant inactivation of cefoxitin (FIG. 3).

AmpC Disk Test

Figure 4:
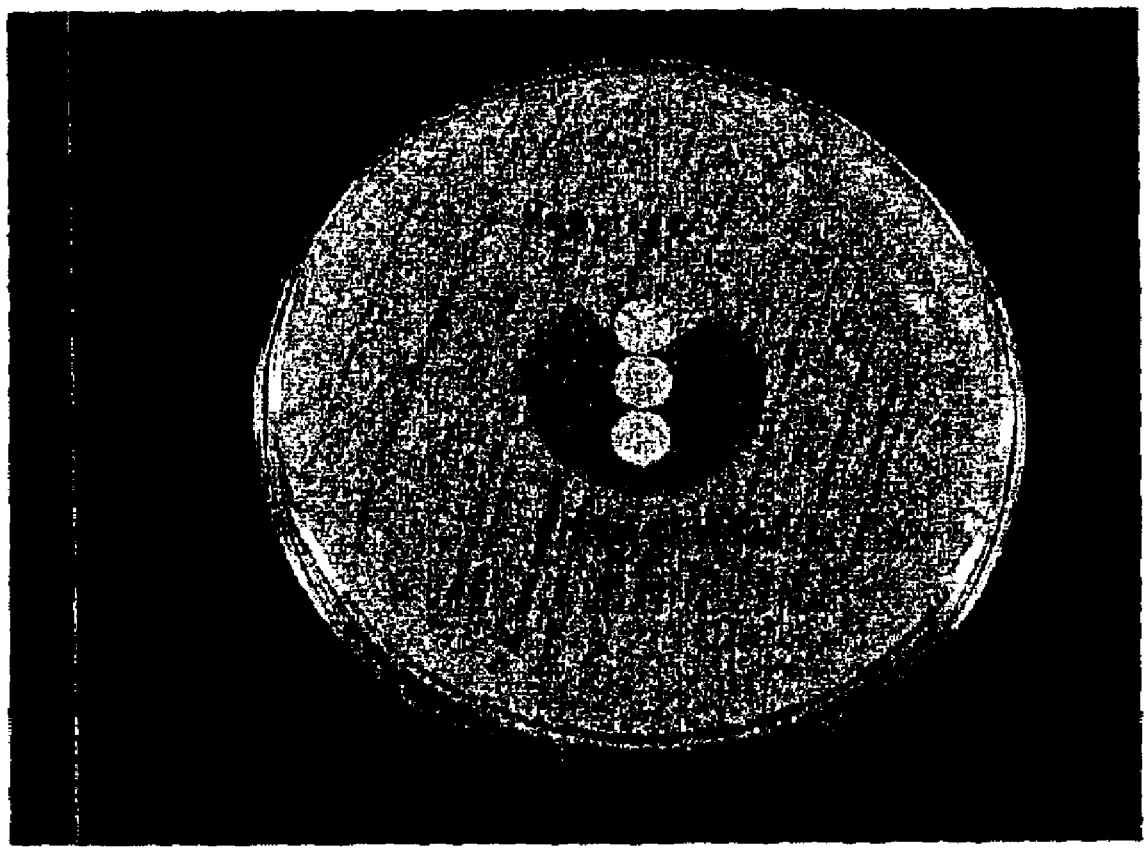
FIG. 4 shows an embodiment of the invention as described above for FIG. 2, except that only a single cefoxitin disk is shown. The portion of FIG. 4 marked "Positive" displays the distorted inhibition zone characteristic of a permeabilizing agent of the invention. The portion of FIG. 4 marked "Negative" displays the lack of distortion where a control reagent disk, not having a permeabilizing agent, is placed proximal to the antibiotic disk.

Enzymatic inactivation of cefoxitin was also investigated by a disk test that used a filter paper disk impregnated with a permeabilizing agent of the invention, TE, as described elsewhere herein. The disk was rehydrated with 20 microliters of sterile saline and then inoculated with several colonies of the test organism. The surface of a Mueller-Hinton agar plate was inoculated with a lawn of a standardized inoculum of *E. coli* ATCC 25922. The inoculated disk was then placed beside a cefoxitin disk (almost touching) on the inoculated plate. After an overnight incubation (about 16 hours) at 35 degrees Celsius, a positive test appeared as a flattening or indentation of the cefoxitin inhibition zone in the vicinity of the test disk. A negative test had an undistorted zone (FIG. 4).

Isoelectric Focusing

Crude sonicates were subjected to analytical isoelectric focusing (IEF) on an ampholine polyacrylamide gel (pH range 3.5-9.5) on a flatbed apparatus (Multiphor LKB). Inhibitor overlays of the IEF gel were performed with 1000 µM clavulanic acid (clavulanate) and cloxacillin.

Results Thirty *Klebsiella* spp. isolates with cefoxitin MICs greater than or equal to 16 µg/ml were tested with the AmpC disk test. Of these, 20 were negative and ten were positive. The negative isolates were confirmed as negative with the three-dimensional test.

IEF and inhibitor studies revealed that nine of the ten positive isolates produced β-lactamases with pIs of either 7.2, 7.7, or 9.0 that were inhibited by cloxacillin. These findings were consistent with AmpC production. These enzymes were interpreted to be plasmid-mediated because *Klebsiella* spp. lack a chromosomal AmpC. The other positive isolate had an elevated imipenem MIC (64 µg/ml) and produced a carbapenem-hydrolyzing enzyme that was also capable of hydrolyzing cefoxitin.

Example 6

Preliminary Data

Preliminary Data Showing Use of a β-Lactamase Inhibitor Added to the Permeabilizer Disk and a Cefoxitin Antibiotic Disk*

| Strain | Enzyme | 5 µg clavulanate | 10 µg clavulanate | 20 µg clavulanate | Saline |
|---|---|---|---|---|---|
| Kleb 265 | KPC-1 | P | N | N | P |
| UMM21 | KPC-2 | P | N | N | P |
| 01IFH73 | CTX-M | NT | N | N | WP |
| 01IFH1white | CTX-M | WP | N | N | WP |
| 01FH15 | CTX-M | WP | N | N | WP |
| Misc 94 | Negative | N | N | N | N |
| HVAMC 39 | Positive-ACT-1 | P | P | Zone | P |

| Strain | Enzyme | 15 µg clavulanate | 10 µg tazobactam | Saline |
|---|---|---|---|---|
| Kleb 265 | KPC-1 | P | P | P |
| UMM21 | KPC-2 | P | P | P |
| UMM30 | KPC-2 | N | N | P |
| UMM12 | KPC-2 | N | P | P |
| 01IFH73 | CTX-M | N | N | P |
| 01IFH1white | CTX-M | N | N | P |
| 01FH15 | CTX-M | N | N | P |
| Misc 94 | Negative | N | N | N |
| HVAMC 39 | Positive-ACT-1 | Zone | P | P |

*Strain: Laboratory code for the bacterial strain.
Enzyme: the type of β-lactamase. The top 5 enzymes are those that yielded a positive result with the AmpC disk test but are not AmpC β-lactamases.
Misc 94 is a β-lactamase negative strain.
The ACT-1 producer is a true AmpC producer.
Results: P, positive; N, negative; WP, weak positive; NT, not tested; Zone, the clavulanate concentration was so high it caused inhibition of the assay strain and the test could not be interpreted. The second disk contained the permeabilizing reagent plus either clavulanate or tazobactam or saline. The saline was a control.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

We claim:

1. A method for determining whether a microorganism produces an AmpC β-lactamase comprising:

a) admixing a culture of a test microorganism with an effective amount of each of
      i) a β-lactam-containing antibiotic,
      ii) a β-lactamase inhibitor to which AmpC β-laetamase is resistant,
      iii) a permeabilizing agent for the microorganism present in a non-growth-inhibiting microorganism-permeabilizing amount to form an assay culture, and
      iv) a strain of microorganism with known susceptibility for said β-lactam-containing antibiotic to form an assay culture; and
   b) maintaining the assay culture under appropriate culture conditions and for a time period sufficient to determine the interaction of the test microorganism with the strain of microorganism, the AmpC β-lactamase resistant inhibitor, and the antibiotic, wherein significant growth of the strain of microorganism or a distortion in a zone of inhibition indicates the production of an AmpC β-lactamase by the test microorganism.

2. The method of claim 1 wherein said β-lactam-containing antibiotic is selected from the group consisting of a cephamycin-, carbapenem-, carbacephem-, monobactam-, penicillin- and a cephalosporin-type antibiotic, or a mixture thereof.

3. The method of claim 1 wherein the β-lactamase inhibitor is present in an amount of about 5 to about 250 µg.

4. The method of claim 1 wherein said permeabilizing agent is dissolved in or dispersed on a carrier.

5. The method of claim 4 wherein said carrier is a solid carrier.

6. The method of claim 5 wherein said solid carrier is a paper disk.

7. The method of claim 4 wherein said carrier is a liquid carrier.

8. The method of claim 4 wherein the permeabilizing agent is a buffer solution.

9. The method of claim 8 wherein said buffer solution is Tris/EDTA.

10. The method of claim 4 wherein said assay culture is provided on a solid growth medium.

11. The method of claim 4 wherein said assay culture is provided in a liquid growth medium.

12. The method of claim 4 wherein said carrier is a solid carrier, said test microorganism is provided on the solid carrier, and said strain of microorganism is provided on a solid growth medium, further wherein said β-lactamase inhibitor is provided on said solid carrier, the β-lactam-containing antibiotic is provided on a solid support, and said admixing is by placing the solid support and the solid carrier on the solid growth medium adjacent each other, whereby, a distortion in a zone of inhibition indicates the production of AmpC β-lactamase by the test microorganism.

13. The method of claim 4 wherein the β-lactamase inhibitor is clavulanate, sulbactam or tazobactam.

14. The method of claim 13 wherein the β-lactamase inhibitor is present in an amount of about 10 to about 30 µg.

15. The method of claim 1, further comprising determining the susceptibility of the test microorganism to the antibiotic based on growth in the assay culture, wherein significant growth of the strain of microorganism is indicative of resistance of the test microorganism to the antibiotic attributable to inactivation of the antibiotic.

* * * * *